(12) United States Patent
Bard et al.

(10) Patent No.: US 9,346,997 B2
(45) Date of Patent: May 24, 2016

(54) LUMINESCENT NANOSTRUCTURED MATERIALS FOR USE IN ELECTROGENERATED CHEMILUMINESCENCE

(71) Applicant: Board of Regents of the University of Texas System, Austin, TX (US)

(72) Inventors: Allen J. Bard, Austin, TX (US); Fu-Ren F. Fan, Austin, TX (US); Khalid Omer, Austin, TX (US)

(73) Assignee: Board of Regents of the University of Texas System, Austin, TX (US)

(*) Notice: Subject to any disclaimer, the term of this patent is extended or adjusted under 35 U.S.C. 154(b) by 91 days.

(21) Appl. No.: 14/327,326

(22) Filed: Jul. 9, 2014

(65) Prior Publication Data

US 2014/0322538 A1    Oct. 30, 2014

Related U.S. Application Data

(62) Division of application No. 13/763,357, filed on Feb. 8, 2013, now Pat. No. 8,815,159, which is a division of application No. 12/990,636, filed as application No. PCT/US2009/002534 on Apr. 24, 2009, now Pat. No. 8,372,652.

(60) Provisional application No. 61/126,892, filed on May 8, 2008, provisional application No. 61/127,311, filed on May 12, 2008.

(51) Int. Cl.
| | |
|---|---|
| *G01N 21/64* | (2006.01) |
| *C09K 11/06* | (2006.01) |
| *B82Y 15/00* | (2011.01) |
| *B82Y 20/00* | (2011.01) |
| *C09K 11/07* | (2006.01) |

(Continued)

(52) U.S. Cl.
CPC ............. *C09K 11/06* (2013.01); *B82Y 15/00* (2013.01); *B82Y 20/00* (2013.01); *C07C 2/64* (2013.01); *C09K 11/07* (2013.01); *G01N 21/64* (2013.01); *G01N 21/66* (2013.01); *G01N 21/76* (2013.01); *C09K 2211/1007* (2013.01); *C09K 2211/1011* (2013.01); *Y10T 428/298* (2015.01); *Y10T 428/2982* (2015.01)

(58) Field of Classification Search
None
See application file for complete search history.

(56) References Cited

U.S. PATENT DOCUMENTS

| | | | |
|---|---|---|---|
| 5,061,445 | A | 10/1991 | Zoski et al. |
| 5,093,268 | A | 3/1992 | Leventis et al. |

(Continued)

FOREIGN PATENT DOCUMENTS

| | | |
|---|---|---|
| CA | 1339465 | 9/1997 |
| WO | WO-87/06706 A1 | 11/1987 |

(Continued)

OTHER PUBLICATIONS

Grabner, E.W., Electrochemiluminescence of rubrene at a zinc oxide electrode, 1975, Electrochimica Acta, vol. 20(1), pp. 7-12.*

(Continued)

*Primary Examiner* — Robert Xu
(74) *Attorney, Agent, or Firm* — Foley & Lardner LLP

(57) ABSTRACT

A nanostructured particulates formed from a redox active, luminescent phenyl substituted polycyclic aromatic hydrocarbon are provided herein. The nanostructured particulates may be used for determining the presence of an analyte of interest in a sample by detecting the emitted electromagnetic radiation generated by exposing a reagent mixture, which includes the nanostructured particulates and the sample, to electrochemical energy.

17 Claims, 8 Drawing Sheets

(51) Int. Cl.
*G01N 21/66* (2006.01)
*G01N 21/76* (2006.01)
*C07C 2/64* (2006.01)

(56) References Cited

U.S. PATENT DOCUMENTS

| | | | |
|---|---|---|---|
| 5,238,808 | A | 8/1993 | Bard et al. |
| 5,296,191 | A | 3/1994 | Hall et al. |
| 5,324,457 | A | 6/1994 | Zhang et al. |
| 5,369,036 | A | 11/1994 | Mercolino et al. |
| 5,527,710 | A | 6/1996 | Nacamulli et al. |
| 5,571,401 | A | 11/1996 | Lewis et al. |
| 5,610,075 | A | 3/1997 | Stahl-Rees |
| 5,679,519 | A | 10/1997 | Oprandy |
| 5,686,244 | A | 11/1997 | Gudibande et al. |
| 5,700,427 | A | 12/1997 | Ghaed et al. |
| 5,705,402 | A | 1/1998 | Leland et al. |
| 5,714,089 | A | 2/1998 | Bard et al. |
| 5,731,147 | A | 3/1998 | Bard et al. |
| 5,786,141 | A | 7/1998 | Bard et al. |
| 5,792,621 | A | 8/1998 | Verostko et al. |
| 5,798,083 | A | 8/1998 | Massey et al. |
| 5,804,400 | A | 9/1998 | Martin et al. |
| 5,811,236 | A | 9/1998 | Massey et al. |
| 5,846,485 | A | 12/1998 | Leland et al. |
| 5,858,676 | A | 1/1999 | Yang et al. |
| 5,866,434 | A | 2/1999 | Massey et al. |
| 5,945,344 | A | 8/1999 | Hayes et al. |
| 6,087,476 | A | 7/2000 | Kenten et al. |
| 6,096,500 | A | 8/2000 | Oprandy et al. |
| 6,120,986 | A | 9/2000 | Martin |
| 6,127,516 | A | 10/2000 | Bard et al. |
| 6,132,648 | A | 10/2000 | Zhang et al. |
| 6,133,043 | A | 10/2000 | Talley et al. |
| 6,136,233 | A | 10/2000 | Jameison et al. |
| 6,136,268 | A | 10/2000 | Ala-Kleme et al. |
| 6,140,138 | A | 10/2000 | Bard et al. |
| 6,146,838 | A | 11/2000 | Williams et al. |
| 6,165,708 | A | 12/2000 | Liang et al. |
| 6,165,729 | A | 12/2000 | Leland et al. |
| 6,271,041 | B1 | 8/2001 | Leland et al. |
| 6,312,896 | B1 | 11/2001 | Heroux et al. |
| 6,316,607 | B1 | 11/2001 | Massey et al. |
| 6,319,670 | B1 | 11/2001 | Sigal et al. |
| 6,325,973 | B1 | 12/2001 | Leland et al. |
| 6,468,741 | B1 | 10/2002 | Massey et al. |
| 6,479,233 | B1 | 11/2002 | Bard et al. |
| 6,517,777 | B2 | 2/2003 | Liljestrand et al. |
| 6,537,498 | B1 | 3/2003 | Lewis et al. |
| 6,613,583 | B1 | 9/2003 | Richter et al. |
| 6,635,418 | B2 | 10/2003 | Heroux et al. |
| 6,702,986 | B1 | 3/2004 | Leland et al. |
| 6,808,939 | B2 | 10/2004 | Sigal et al. |
| 6,846,629 | B2 | 1/2005 | Sigal et al. |
| 6,852,502 | B1 | 2/2005 | Martin |
| 6,881,536 | B1 | 4/2005 | Shah et al. |
| 6,890,712 | B1 | 5/2005 | Kenten et al. |
| 6,972,173 | B2 | 12/2005 | Su et al. |
| 7,018,802 | B2 | 3/2006 | Martin et al. |
| 7,022,287 | B2 | 4/2006 | Schoeniger et al. |
| 7,160,735 | B2 | 1/2007 | Dehlinger et al. |
| 7,176,036 | B2 | 2/2007 | Wang et al. |
| 7,314,711 | B2 | 1/2008 | Richter et al. |
| 7,517,701 | B2 | 4/2009 | Parker et al. |
| 7,553,448 | B2 | 6/2009 | Kumar et al. |
| 7,682,788 | B2 | 3/2010 | Sigal et al. |
| 8,044,390 | B2 | 10/2011 | Hosokawa et al. |
| 8,106,391 | B2 | 1/2012 | Endo et al. |
| 8,367,002 | B2 * | 2/2013 | Ibanez .............. B82Y 15/00 422/82.08 |
| 2003/0059839 | A1 | 3/2003 | Obiso et al. |
| 2004/0058389 | A1 | 3/2004 | Wang et al. |
| 2004/0067503 | A1 | 4/2004 | Tan et al. |
| 2004/0096368 | A1 | 5/2004 | Davis et al. |
| 2004/0175742 | A1 | 9/2004 | Hofmann et al. |
| 2005/0084881 | A1 | 4/2005 | Kelley et al. |
| 2005/0214565 | A1 | 9/2005 | Ikeda et al. |
| 2006/0078912 | A1 | 4/2006 | Bard et al. |
| 2007/0034529 | A1 | 2/2007 | Bard et al. |
| 2007/0048477 | A1 | 3/2007 | Oh |
| 2007/0131937 | A1 | 6/2007 | Oh |
| 2007/0141727 | A1 | 6/2007 | Huang et al. |
| 2008/0157403 | A1 | 7/2008 | Lee et al. |
| 2009/0065371 | A1 | 3/2009 | Xiao et al. |
| 2010/0140086 | A1 | 6/2010 | Sigal et al. |
| 2010/0187512 | A1 | 7/2010 | Ito |
| 2010/0219404 | A1 | 9/2010 | Endo et al. |
| 2010/0283043 | A1 | 11/2010 | Nishimura et al. |
| 2010/0289013 | A1 | 11/2010 | Ito et al. |
| 2010/0295029 | A1 | 11/2010 | Kawamura |
| 2010/0295030 | A1 | 11/2010 | Kawamura |
| 2010/0301312 | A1 | 12/2010 | Jinde et al. |
| 2010/0301313 | A1 | 12/2010 | Ito et al. |
| 2010/0320451 | A1 | 12/2010 | Kawamura |
| 2010/0320452 | A1 | 12/2010 | Kawamura |
| 2010/0327266 | A1 | 12/2010 | Kawamura |
| 2011/0001130 | A1 | 1/2011 | Nishimura et al. |
| 2011/0017983 | A1 | 1/2011 | Mizuki et al. |

FOREIGN PATENT DOCUMENTS

| | | |
|---|---|---|
| WO | WO-92/14139 | 8/1992 |
| WO | WO-92/14139 A1 | 8/1992 |
| WO | WO-96/21154 A1 | 7/1996 |
| WO | WO-96/35697 A1 | 11/1996 |
| WO | WO-03/089906 A2 | 10/2003 |
| WO | WO-2005/062982 | 7/2005 |
| WO | WO 2008/145875 A1 | 12/2008 |
| WO | WO-2009/057430 | 5/2009 |
| WO | WO-2009/126249 | 10/2009 |

OTHER PUBLICATIONS

Fu, H., et al. Multiple Emissions from 1,3-Diphenyl-5-pyreny1-2-pyrazoline Nanoparticles: Evolution from Molecular to Nanoscale to Bulk Materials, 2002, Angew. Chem., vol. 114(6), pp. 1004-1007.*
Abstract of JP 06-300763, publication date Oct. 28, 1994, 1 page.
Abstract of JP 09-184841, publication date Jul. 15, 1997, 1 page.
Abstract of JP 09-184842, publication date Jul. 15, 1997, 2 pages.
Abstract of JP 2004-361334, publication date Dec. 24, 2004, 1 page.
An et al., Enhanced Emission and Its Switching in Fluorescent Organic Nanoparticles, J. Am. Chem. Soc., May 15, 2002, pp. 14410-14415, vol. 124, No. 48.
Bae et al., Electrochemistry and Electrogenerated Chemiluminescence of CdTe Nanoparticles, Nano Letters, 2004, pp. 1153-1161, vol. 4, No. 6.
Bard et al., Electrochemistry and Electrogenerated Chemiluminescence of Semiconductor Nanocrystals in Solutions and in Films, Struc Bond, Sep. 23, 2005, pp. 1-57, vol. 118.
Chang et al., Electrogenerated Chemiluminescence of Single Conjugated Polymer Nanoparticles, J. Am. Chem. Soc., May 9, 2008, pp. 8906-8907, vol. 130, No. 28.
Chen, Gold Nanoparticle-Modified ITO Electrode for Electrogenerated Chemiluminescence: Well-Preserved Transparency and Highly Enhanced Activity, Langmuir, 2007, pp. 11387-11390, vol. 23, No. 23.
Chovin et al., Development of an Ordered Microarray of Electrochemiluminescence Nanosensors, Measurement of Science and Technology, May 1, 2006, pp. 1211-1219, vol. 17, No. 5.
Cui et al., Multichannel Electrochemiluminescence of Luminol in Neutral and Alkaline Aqueous Solutions on a Gold Nanoparticle Self-Assembled Electrode, Analytical Chemistry, Jul. 15, 2004, pp. 4002-4010, vol. 76, No. 14.
Cui et al., Multichannel Electrogenerated Chemiluminescence of Lucigenin in Neutral and Alkaline Aqueous Solutions on a Gold Nanoparticle Self-Assembled Gold Electrode, Journal of ElectroAnalytical Chemistry, Jul. 25, 2006, pp. 37-46, vol. 595.
Ding et al., Electrochemistry and Electrogenerated Chemiluminescence from Silicon Nanocrystal Quantum Dots, Science Magazine, May 17, 2002, pp. 1293-1297, vol. 296.

(56) References Cited

OTHER PUBLICATIONS

Fan et al., An Electrochemical Coulomb Staircase: Detection of Single Electron-Transfer Events at Nanometer Electrodes, Science Magazine, Sep. 19, 1997, 3 pages, vol. 277.

Fan et al., Observing Single Nanoparticle Collisions by Electrogenerated Chemiluminescence Amplification, Nano Letters, May 21, 2008, pp. 1746-1749, vol. 8, No. 6.

Fraser et al., "Synthesis of Halomethyl and Other Bipyridine Derivatives by Reaction of 4,4'-Bis (trimethylsilyl0methyl]-2,2'-bipyridine with Electophiles in the Presence of Fluoride Ion," J Orgn. Chem, 1997, vol. 62, pp. 9314-9317, 5 pages with cover sheet.

Fu et al., "Size Effects on the Optical Properties of Organic Nanoparticles," J Am Chem Soc, 2001, vol. 123, pp. 1434-1439.

Fu et al., Multiple Emissions for 1,3-Diphenyl-5-pyrenyl-2-pyrazoline Nanoparticles: Evolution from Molecular to Nanoscale to Bulk Materials, Angew. Chem. Int. Ed., 2002, pp. 962-965, vol. 41, No. 6.

Gill et al., "Pt Nanoparticles Functionalized with Nucleic Acid Act as Catalytic Labels for the Chemiluminescent Detection of DNA and Proteins," Small, 2006, vol. 2, pp. 1037-1041, 7 pages with cover sheets.

Grey et al., Size-Dependent Spectroscopic Properties of Conjugated Polymer Nanoparticles, J. Phy. Chem., Nov. 30, 2006, pp. 25568-25572, vol. 110, No. 51.

Guo et al., A New Electrogenerated Chemiluminescence Peak of Lucigenin in the Hydrogen-Evolution Region Induced by Platinum Nanoparticles, J. Phys. Chem. C, Dec. 2, 2006, pp. 606-611, vol. 111, No. 2.

He et al., Photostable Luminescent Nanoparticles as Biological Label for Cell Recognition of System Lupus Erythematosus Patients, Journal of Nanoscience and Nanotechnology, 2002, vol. 2, No. 3/4, pp. 317-320.

Henglein et al., Absorption Spectrum and Some Chemical Reactions of Colloidal Platinum in Aqueous Solution, J. Phys. Chem., Jul. 12, 1995, pp. 14129-14136, vol. 99, No. 38.

Hongbing Fu et al., Multiple Emissions from 1,3-Diphenyl-5-pyrenyl-2-pyrazoline Nanoparticles: Evolution from Molecular to Nanoscale to Bulk Materials, Angew. Chem. 2002, 114, Nr. 6, pp. 1004-1007.

International Search Report and Written Opinion for PCT/US2009/002534, mail date Dec. 15, 2009, 16 pages.

Kang et al., "Colloid Chemical Reaction Route to the Preparation of Nearly Monodispersed Perylene Nanoparticles: Size-Tunable Synthesis and Three-Dimensional Self-Organization," J Am Chem Soc, 2007, vol. 129, pp. 7305-7312.

Kasai et al., "Optical Properties of Perylene Microcystals," Mol. Cryst. Liq. Cryst., 1997, vol. 294, pp. 173-176.

Kasai et al., A Novel Preparation Method of Organic Microcrystals, Jpn. J. Appl. Phys., Aug., 1992, pp. L 1132-L 1134, Part 2, No. 8A.

Kasai et al., Crystal. Size Dependence of Emission from Perylene Microcrystals, Chemistry Letters, Jul. 11, 1997, pp. 1181-1182.

Kwon et al., "Surface structure effect on optical properties of organic nanocystals", Chemical Physics Letter, 2007, vol. 441, 5 pages.

Miao et al., Electrogenerated Chemiluminescence. 72. Determination of Immobilized DNA and C-Reactive Protein on Au(111) Electrodes Using Tris (2,2'-bipyridyl)ruthenium(II) Labels, Analytical Chemistry, Nov. 1, 2003, pp. 5825-5834, vol. 75, No. 21.

Miao et al., Electrogenerated Chemiluminescence. 77. DNA Hybridization Detection at High Amplification with [Ru(bpy)3]2 -Containing Microspheres, Analytical Chemistry, Sep. 15, 2004, pp. 5379-5386, vol. 76, No. 18.

Miao et al., Electrogenerated Chemiluminescence. 80. C-Reactive Protein Determination at High Amplification with [Ru(bpy)3]2 -Containing Microspheres, Analytical Chemistry, Dec. 1, 2004, pp. 7109-7113, vol. 76, No. 23.

Myung et al., Electrogenerated Chemiluminescence of CdSe Nanocrystals, Nano Letters, Oct. 22, 2002, pp. 1315-1319, vol. 2, No. 11.

Myung et al., Electrogenerated Chemiluminescence of GE Nanocrystals, Nano Letters, Dec. 5, 2003, pp. 183-185, vol. 4, No. 1.

Niazov et al., "Photoswitchable Electrocatalysis and Catalyzed Chemiluminescence Using Photoisomedzable Monolayer-Functionalized Surfaces and Pt Nanoparticles," J Am Chem Soc, 2007, vol. 129, pp. 6374-6375, 4 pages with cover sheets.

Omer et al., Electrochemistry and Electrogenerated Chemiluminescense of a Spirobiflourene-Based Donor (Triphenylamine)-Acceptor (2,1,3-Benzothiadiazole) Molecule and Its Organic Nanoparticles, Journal of the American Chemical Society, 2011, 133, pp. 5492-5499, 8 pages.

Omer et al., Electrogenerated Chemiluminescence of Aromatic Hydrocarbon Nanoparticles in an Aqueous Solution, J. Phys. Chem., Apr. 7, 2009, 4 pages, vol. 113.

Omer et al., Electrogenerated Chemiluminescence of Aromatic Hydrocarbon Nanoparticles in an Aqueous Solution, J. Phys. Chem., Apr. 7, 2009, 4 pages, vol. xxx, No. xx.

Palacios et al., "Single Molecule Spectroelectrochemistry (SMS-EC)," J Am Chem Soc, 2006, vol. 128, pp. 9028-9029.

Palacios et al., Charging and Discharging of Single Conjugated-Polymer Nanoparticles, Nature Materials, Sep. 2007, pp. 680-685, vol. 6.

Polsky et al., "Nucleic Acid-Functionalized Pt Nanoparticles: Catalytic Labels for the Amplified Electrochemical Detection of Biomolecules," Anal. Chem,. 2006, vol. 78, pp. 2268-2271, 6 pages with cover sheets.

Richiter et al., Electrochemistry and electrogenerated chemiluminescence of films of the conjugated polymer 4-methoxy-(2-ethylhexoxyl)-2, 5-polyphenylenevinylene, Chemical Physics Letters, 1994, vol. 226, pp. 115-120.

Richter, Electrochemical Light, From Laboratory Curiosity to Useful Analytical Technique, Chem. Educator 2002, 7, 195-199.

Sonnichsen et al., "A Molecular Ruler Based on Plasmon Coupling of Single Gold and Silver Nanoparticles," Nature Biotechnology, 2005, vol. 23, pp. 741-745, 7 pages with cover sheets.

Szymanski et al., Single Molecule Nanoparticles of the Conjugated Polymer MEH-PPV, Preparation and Characterization by Near-Field Scanning Optical Microscopy, J. Phys. Chem., Apr. 9, 2005, pp. 8543-8546, vol. 109, No. 18.

Tel-Vered et al., Generation and Detection of Single Metal Nanoparticles Using Scanning Electrochemical Micrscopy Techniques, J. Phys. Chem, B, vol. 110, No. 50, 2006, pp. 25279-25287, 9 pages.

The Center for Electrochemistry, The University of Texas at Austin Newsletter, available at least by Nov. 6, 2008, 2 pages.

Wilson et al., Comparison Between Acridan Ester, Luminol, and Ruthenium Chelate Electrochemiluminescence, Electronoanalysis, 2001, pp. 1083-1092, vol. 13, No. 13.

Xiao et al., "Measurement of Single Molecule Conductance: Benzenedithiol and Benzenedimethanethiol," Nano Letters, 2004, vol. 4, pp. 267-271, 7 pages with cover sheets.

Xiao et al., "Observing Single Nanoparticle Collisions at an Ultramicroelectrode by Electrocatalytic Amplification," J Am Chem Soc, 2007, vol. 129, pp. 9610-9612.

Xiao et al., Current Transients in Single Nanoparticle Collision Events, J. Am. Chem. Soc., Nov. 19, 2008, pp. 16669-16677, vol. 130, No. 49.

Xiao et al., Observing Single Nanoparticle Collisions at an Ultramicroelectrode by Electrocatalytic Amplification, J. Am Chem. Soc., Jul. 14, 2007, pp. 9610-9612, vol. 129, No. 31.

Xi-Cun Gao et al., Properties of a new pyrazoline derivative and its application in electroluminescence, Journal of Materials Chemistry, 1999, 9, pp. 1077-1080.

Yang et al., "Size effect in thiol and amine binding to small Pt nanoparticles," Analytica Chimica Acta, 2006, vol. 571, pp. 206-210.

Yu et al., Spontaneous Formation and Electrogenerated Chemiluminescence of Tri(bipyridine) Ru(II) Derivative Nanobelts, J. Am Chem. Soc., Feb. 27, 2008, pp. 7196-7197, vol. 130, No. 23.

Zhang et al., "Single-Crystal 9, 10-diphenylanthracene Nanoribbons and Nanorods," Chem. Mater., 2008, vol. 20, pp. 6945-6950.

Zhang et al., Single-Crystal Nanoribbons, Nanotubes, and Nanowires from Intramolecular Charge-Transfer Organic Molecules, J. Am. Chem. Soc., Jun. 15, 2006, pp. 3527-3532, vol. 129, No. 12.

(56) References Cited

OTHER PUBLICATIONS

Zhou et al., "Scanning electrochemical microscopy Part 39. The proton:hydrogen mediator system and its application to the study of the electrocatalysis of hydrogen oxidation," J Electroanal Chem, 2000, vol. 491, 11 pages.

Zu et al., Electrogenerated Chemiluminescence. 66. The Role of Direct Coreactant Oxidation in the Ruthenium Tris(2,2')bipyridyl/Tripropylamine System and the Effect of Halide Ions on the Emission Intensity, Analytical Chemistry, Jul. 15, 2000, pp. 3223-3232, vol. 72, No. 14.

Buda, M. et al. Electrochemistry and electrogenerated chemiluminescence of a thin solid film of a hydrophobic tris(bipyridine) Ru(II) derivative in contact with an aqueous solution, 2004, Journal of Solid State Electrochemistry, vol. 8, pp. 706-717.

Botzung-Appert, E. et al., Polyaromatic Luminescent Nanocrystals for Chemical and Biological Sensors, Chem. Mater., vol. 16, No. 9, 2004 (published on Web Apr. 8, 2004), pp. 1609-1611.

Monnier, V., et al., Confined nucleation and growth of organic nanocrystals in sol-gel matrices, J. Mater. Chem., vol. 16, 2006 (published as advance article on the Web on Feb. 1, 2006), pp. 1401-1409.

\* cited by examiner

LUMINESCENT NANOSTRUCTURED MATERIALS FOR USE IN ELECTROGENERATED CHEMILUMINESCENCE

CROSS-REFERENCE TO RELATED APPLICATIONS

This patent application is a divisional application of U.S. patent application Ser. No. 13/763,357, filed on Feb. 8, 2013, which is a divisional application of U.S. patent application Ser. No. 12/990,636 (issued as U.S. Pat. No. 8,372,652), which is a national stage of International Patent Application No. PCT/US2009/002534, filed on Apr. 24, 2009; PCT Application No. PCT/US2009/002534 claims the benefit of U.S. Provisional Patent Application 61/126,892, filed on May 8, 2008, and U.S. Provisional Patent Application 61/127,311, filed on May 12, 2008; the entire contents of all of these earlier filed applications are hereby incorporated by reference, for any and all purposes.

BACKGROUND

Nanoparticles ("NPs") have been reported to have a wide range of applications in electronics, optics, catalysis and biotechnology. The physical properties (e.g., high surface-to-volume ratio, elevated surface energy, increased ductility after pressure loading, higher hardness, larger specific heat and the like) of NPs have led to a variety of applications in the material-directed industry and material science. For example, a variety of metal NPs have been used to catalyze numerous reactions and semiconductor NPs are used as fluorescent probes.

Single particle electrochemical sensors, which employ an electrochemical device for detecting single particles, have also been reported. Methods for using such a device to achieve high sensitivity for detecting particles such as bacteria, viruses, aggregates, immuno-complexes, molecules, or ionic species have been described.

The use of colloidal particles in sensing arrays have also been reported. These are chemical sensors for detecting analytes in fluids via arrays having a plurality of alternating nonconductive regions and conductive regions of conductive NP materials. Variability in chemical sensitivity from sensor to sensor is reported to be provided by qualitatively or quantitatively varying the composition of the conductive and/or nonconductive regions.

The size of nanostructured materials ("NSMs") generally ranges from less than 1 nm to several hundred nm at least in one dimension and the electronic energy band configuration is a size-dependent property, which in turn can affect the physical and chemical properties. A fundamental distinction between NSMs and bulk materials is that the fraction of surface atoms and the radius of curvature of the surface of NSMs are comparable with the lattice constant. As a result, nanostructured materials generally have higher activity as compared with their analogues based on bulk materials. A number of methods of forming NSMs are known to the skilled artisan and include formation by combining atoms (or more complex radicals and molecules) and by dispersion of bulk materials, e.g., thermal evaporation, ion sputtering, reduction from solution, reduction in microemulsions, and condensation.

SUMMARY

The present application relates, in general, to the field of nanostructured materials, such as nanoparticles (NPs), including the synthesis and characterization of organic and/or ionic luminescent nanostructured materials. Such nanostructured materials ("NSMs") formed from luminescent organic and/or ionic materials may be employed for electrogenerated chemiluminescence (ECL). The difficulties in generating, locating and characterizing NPs, especially at the nm scale and in measuring the very small current and ECL intensity generated by the electrode reactions at NPs has been recognized. The present application provides a method and apparatus, which can be used for observing the ECL generated during the collisions of nanostructured materials at the electrode. The present method can provide information with respect to the electrochemical processes of the nanostructured materials, as well as provide the basis for highly sensitive electroanalytical methods. The electrochemical properties measured in the present method can be any property that can be measured by the apparatus; however, the most common property involves ECL generation from a redox reaction of the nanostructured materials. Another commonly monitored property can be a current.

The present device commonly includes an electrochemical cell in a sample chamber. The electrochemical cell typically has two or more electrodes, one or more ports for introducing nanostructured materials into the sample chamber, and an electrochemical apparatus in communication with the electrodes. The electrochemical cell may be connected to a measuring apparatus which includes an electrochemical apparatus and a photon detector. The injected nanostructured materials can interact with the electrode and generate one or more photons that can be picked up by a photon detector.

The present invention includes a kit for analyzing one or more chemical analyte(s) having at least one ECL NSM, at least two electrodes, an optional co-reactant and a measuring apparatus that reads one or more of current and ECL properties generated by the interactions between the NSM(s), the electrode(s) and the chemical analyte(s).

One embodiment provides a method for detecting an analyte in a sample solution to which luminescent nanostructured materials have been added. The method includes introducing the sample solution into an electrochemical cell containing two or more electrodes in communication with the solution; generating one or more ECL properties through an interaction of the luminescent nanostructured materials, the liquid sample and one or more of the electrodes; and measuring at least one ECL property generated by the interaction. The luminescent nanostructured materials include a redox active, luminescent organic and/or ionic compound. A coreactant may be added to the liquid sample to enhance the generation of the ECL properties. Examples of suitable coreactants include oxalate salts (e.g., sodium oxalate), persulfate, benzoyl peroxide and trialkyl amines (e.g., tripropyl amine).

One embodiment provides a method for detecting an analyte in a sample solution to which a plurality of luminescent nanostructured materials have been added. The method includes introducing the sample solution into an electrochemical cell containing two or more electrodes in communication with the solution; generating one or more ECL properties through an interaction of the luminescent nanostructured materials, the liquid sample and one or more of the electrodes; and measuring at least one ECL property generated by the interaction. The luminescent nanostructured materials include a redox active, luminescent organic and/or ionic compound.

Another embodiment provides a method for observing interaction of a nanostructured material with an electrode surface comprising:

contacting a dispersion of luminescent nanostructured materials in a liquid sample with one or more electrodes;

exposing the dispersion to electrochemical energy through the one or more electrodes;

measuring at least one ECL property generated by an interaction of a luminescent nanostructured material with one of the electrodes. Measuring the ECL property(s) may include measuring an electrochemical property, such as a current, generated by the interaction. Measuring the ECL property(s) may include measuring an optical property, such as ECL, generated by the interaction. Measuring the ECL property(s) may include measuring one or more ECL properties generated by an interaction of a luminescent nanostructured material with a surface of one of the electrodes. The dispersion is typically an aqueous colloid solution of nanostructured materials, which are formed from a redox active, luminescent organic or organometallic compound.

BRIEF DESCRIPTION OF THE DRAWINGS

For a more complete understanding of the features and advantages of the present compositions, methods and devices, reference is now made to the detailed description there along with the accompanying FIGS, and in which:

(FIG. 3A and FIG. 3B) 5 min. (FIG. 3C) 30 min. (FIG. 3D) 2 hours. ([Ru-LCE]=$1.35 \times 10^{-5}$ M, pH 7.0).

DETAILED DESCRIPTION

Figure 1:
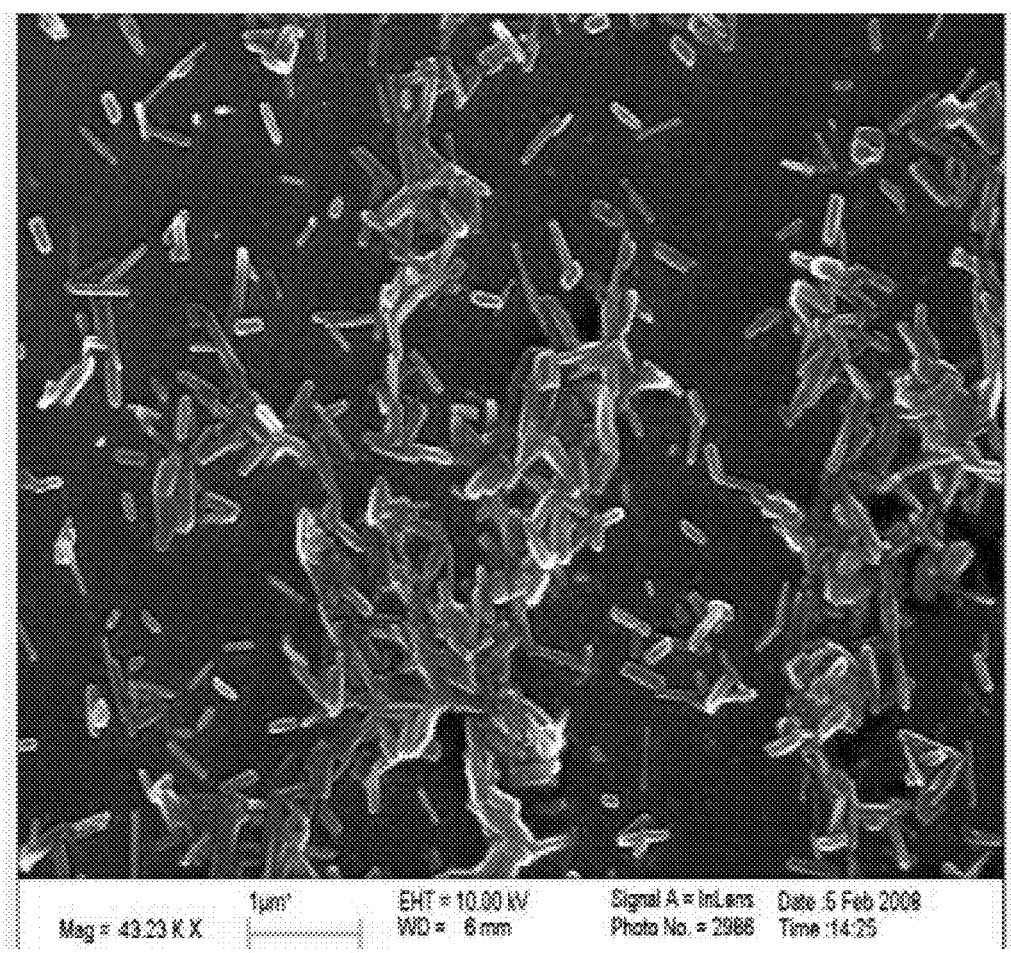
FIG. 1 shows an SEM image of 9,10-diphenylanthracene ("DPA") nanorods.

Methods, apparatus and kits for analyzing a chemical analyte using an electrochemical cell connected to a measuring apparatus are provided herein. The electrochemical cell contains a solution which includes one or more redox active luminescent nanostructured materials, one or more chemical analytes, and optionally, coreactant. In addition, the electrochemical cell contains two or more electrodes in electrical communication with the solution. Two or more ECL properties are generated by the interaction of the luminescent nanostructured materials and the liquid sample and measured at one or more of the electrodes.

By modifying the particle concentration, particle size and concentration of the co-reactant (if a co-reactant is used), i-t profiles and/or ECL intensity vs. time curves may be used to obtain information about the reaction kinetics of indicator and co-reactant. In comparison to optical, conductivity and mass signals using nanostructured materials, the present nanoparticle-based ECL technique can permit detection with a simple apparatus at high sensitivity.

The present application includes methods, compositions and kits for analyzing a chemical analyte having an electrochemical cell connected to a measuring apparatus. The electrochemical cell contains a solution having one or more nanostructured materials, with or without co-reactant. In addition, the electrochemical cell contains two or more electrodes in communication with the solution. One or more emission events are generated by the interaction of the one or more nanostructured materials and the co-reactant (if the co-reactant is present) and measured at the electrodes or an optical detector connected to the cell.

The present application provides devices which may include one or more redox active luminescent nanostructured materials in solution within the electrochemical cell. For example, the one or more redox active luminescent nanostructured materials may be ionic nanostructured materials (e.g., formed from a organometallic compounder nanostructured materials of small organic compounds or polymers. The nanostructured materials may be of a size between about 1 nm and less than about 1000 nm, at least in one dimension. Furthermore, the size distribution of nanostructured material may be generally uniform, disperse, or varying. The nanostructured materials may have different groups of particles that have generally similar size within the group but differing size relative to other groups in the solution. For example, in many embodiments the nanostructured particulates have a least one dimension which has an average size no larger than about 250 nm and, in some instances, no larger than about 100 nm. The nanostructured particulates may be of a size and shape such that no average dimension is larger than about 500 nm.

The present application provides methods for the preparation of nanostructured materials including organic and/or ionic luminescent compounds. Examples of suitable organic luminescent compounds may include luminescent aromatic compounds, e.g., luminescent polycyclic aromatic hydrocarbons. Examples of suitable ionic luminescent compounds which may be employed in the present methods include luminescent metal-containing complexes, e.g., polydentate complexes of a metal ion. Suitable metals which may be included in such compounds include ruthenium, osmium, rhenium, iridium, platinum, cerium, europium, terbium, and/or ytterbium. Ruthenium-containing organometallic compounds are commonly employed in the present nanostructured materials and methods. The methods also include embodiments, where the nanostructured material includes luminescent nanoparticles formed from luminescent phenyl substituted, polycyclic aromatic hydrocarbons, such as rubrene and diphenylanthracene (DPA).

As used herein, the phrase "nanostructured material" refers to materials that have a bulk structure on the nano-scale, i.e., have at least one dimension which is no larger than about 250 nm. In other words, when the materials are in the solid state, crystals or materials of given structure are formed from the compounds that comprise the bulk material. Nanostructured materials, as used herein, are not individual compounds.

The metal-containing organic compound includes polydentate ligands, e.g., heteroaromatic polydentate ligands such as bipyridyl, substituted bipyridyl, 1,10-phenanthroline and/or substituted 1,10-phenanthroline, where one or more of the polydentate ligands includes at least one long chain hydrocarbon group, e.g., a linear long chain alkyl group typically having from 12 to 22 carbon atoms. For example, the metal-containing organic compounds include compounds of the formula $[M(PD)_2(C(O)O(CH_2)_nCH_3)_2\text{-PD})]X_2$, where PD is a polydentate ligand; M is a metal ion, such as a Ru or Os ion; n is an integer from 10 to 30; and X is an anion. Exemplary compounds where M is Ru and PD is a bipyridyl (bpy) group, may have the following formula, referred to Ru-LCE, which refers to a ruthenium compound having a long chain alkyl group attached as an ester, hence the term LCE (long chain ester):

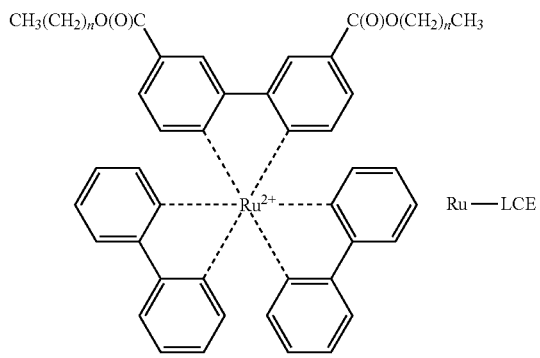

Ru—LCE

Specific examples of suitable ECL moieties include compounds which include at least one long chain alkyl substituted bis(2,2'-bipyridyl)ruthenium(II) or tris(2,2'-bipyridyl)ruthenium(II) moiety. One group of such compounds which can act as an ECL label are long chain alkyl substituted $Ru(bpy)_3^{2+}$ salts, e.g., $Ru(bpy)_2(4,4'-(C(O)O(CH_2)_nCH_3)_2\text{-bpy}) Cl_2$ and $Ru(bpy)_2(4,4'-(C(O)O(CH_2)_nCH_3)_2\text{-bpy})(ClO_4)_2$, where n is an integer from 10 to 30. Specific examples include $Ru(bpy)_2(4,4'-(C(O)O(CH_2)_{14}CH_3)_2\text{-bpy})^{2+}$ salts (also referred to herein as "$Ru(bpy)_2(bpy-C_{16}Est)^{2+}$ salts").

Other suitable examples of long chain alkyl substituted $Ru(bpy)_3^{2+}$ salts include compounds such as $Ru(bpy)_2(LCsub-bpy)^{2+}$ salts, where the "LCsub-bpy" ligand is a long chain alkyl substituted bipyridyl compound. Long chain alkyl substituted bipyridyl compounds can be prepared by a number of methods known to those of skill in the art. Examples include the product of reaction of metal bis(2,2'-bipyridine)(4-methyl-4'-aminomethyl-2,2'-bipyridine) salts with an activated carboxylic acid, such as stearoyl chloride or other activated long chain alkanoic acid derivative (e.g., $CH_3(CH_2)_nCO_2$—X, where n is an integer from about 10 to 25), to form the corresponding diamide. Ru(II) bis(2,2'-bipyridine)(4-methyl-4'-aminomethyl-2,2'-bipyridine salts are also referred to herein as "$Ru(bpy)_2(bpy-C_{19}Amd)^{2+}$ salts". Examples of synthetic methods to produce long chain alkyl substituted bipyridines are described in U.S. Pat. Nos. 5,324,457 and 6,808,939 and Fraser et al, J. Org. Chem., 62, 9314-9317 (1997), the disclosures of which are herein incorporated by reference.

Long chain alkoxy substituted bipyridines can be produced by reaction of a long chain alkoxide (e.g., $NaO(CH_2)_nCH_3$, where n is an integer from about 10 to 25) with 4,4'-bis-bromomethylbipyridine.

Long chain alkyl mercaptan substituted bipyridines can be produced by reaction of a long chain alkyl mercaptan (e.g., $NaS(CH_2)_nCH_3$ where n is an integer from about 10 to 25) with 4,4'-bis-bromomethylbipyridine.

Long chain alkoxy substituted bipyridines can be produced by reaction of a long chain alkyl halide (e.g., $Br(CH_2)_nCH_3$, where n is an integer from about 10 to 25.) with 4,4'-bis-hydroxymethyl-2,2'-bipyridine. For example, see U.S. Pat. No. 6,808,939.

Long chain alkyl ester substituted bipyridines can be produced by esterification of 4-(4-methyl-2,2-bipyridine-4'-yl)-butyric acid with a long chain alkanol (e.g., $HO(CH_2)_nCH_3$ where n is an integer from 6 to 25). For example, see U.S. Pat. No. 6,808,939.

Long chain alkyl ester substituted bipyridines can also be produced by esterification of 4,4'-bis-(carboxy)bipyridine with long chain fatty alcohols, such as stearyl alcohol.

The metal-containing organic complexes including polydentate ligands (e.g., bipyridyl ligands) described above can include one or more of a number of different metal ions so long as the complex is luminescent. As noted above, examples of suitable metal ions which may be employed in such complexes include ruthenium, osmium, rhenium, cerium, europium, terbium, and/or ytterbium ions. Such compounds may variously be known as coordination compounds or organometallic compounds. As used herein, organometallic compounds are those compounds having a metal and an organic group, although no direct metal-carbon bond may be present in the complex, although "organometallic" also refers to compounds with a metal-carbon bond. Coordination compounds are well known to those of skill in the art.

The nanoparticles employed in the methods described herein can be produced by a variety of methods known to those of skill in the art. For example, nanoscale structures of organic and/or ionic luminescent compounds may be produced from a solution of a luminescent compound in a suitable solvent for the compound, and then, typically under vigorous mixing, adding the first solution into an anti-solvent for the compound. The first solution may be injected rapidly or added in a dropwise manner in to the anti-solvent. This "re-precipitation method" may be conducted with or without the presence of a capping agent, such as a low molecular weight surfactant, e.g., Triton X-100, a neutral charge polymer or a charged polymer. For certain embodiments, it may be advantageous to form nanoparticles by introducing a solution a solution of the luminescent compound in an organic solvent into an aqueous solution that is free of any added surfactant. The presence of surfactant may have a negative effect on the generation of ECL using the resultant nanoparticles, possibly due to the presence of a layer of surfactant on the outside of the nanoparticles. As employed herein, the term "substantially free of surfactant" refers to nanoparticles that have been prepared from a mixture of organic solvent and aqueous solution that contains no added surfactant.

Specific examples of the production of nanoscale structures of organic compounds formed by re-precipitation methods are described in Kasai et al., *Jpn. J. Appl. Phys.* (1992), 31, 1132, the disclosure of which is herein incorporated by reference. Examples of suitable solvents which may be employed in such re-precipitation methods include polar, water miscible organic solvents such as acetonitrile (MeCN), acetone (MeCOMe), tetrahydrofuran (THF), N,N-dimethyl-formamide (DMF) and the like. Water is commonly employed as the poor solvent in forming the present nanostructured materials, although other solvents, e.g., hexane, can also be employed as the poor solvent.

Without being bound by theory, it is believed that the general scheme depicted in Scheme I below provides an illustration of the basic mechanism by which an emitting excited state of an electrochemiluminescent moiety is generated. As depicted, radical species having one more or one less electron (in reference to their normal state) are generated and subsequently can combine to create an excited state of the chemiluminescent moiety.

Scheme I

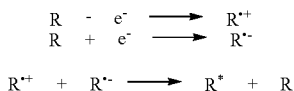

Ru-LCE nanobelts (NBs) were synthesized by a simple re-precipitation method from a 4% w/v solution in MeCN at room temperature. Such Ru-LCE NBs are typically insoluble in water, but are soluble in polar organic solvents that are miscible with water. For example, [Ru(bpy)$_2$(4,4'-(C(O)O(CH$_2$)$_{14}$CH$_3$)$_2$-bpy)]$^{2+}$ is insoluble in water, but is very soluble in either acetonitrile or acetone. In a typical preparation, 4 μL of this solution was rapidly injected into 10 mL of highly pure (Millipore) water under ultrasonic agitation at room temperature for 30 s, followed by aging in a closed vial at room temperature for 24 h. The resulting colloid solution is a transparent orange-yellowish solution that exhibits strong light scattering, confirming the formation of nanoparticles. With increasing aging time (a month), a small amount of orange-yellow nanobelt precipitate settled. The nanobelts can easily be dispersed and a clear solution can be re-obtained by slight agitation.

Figure 2A:
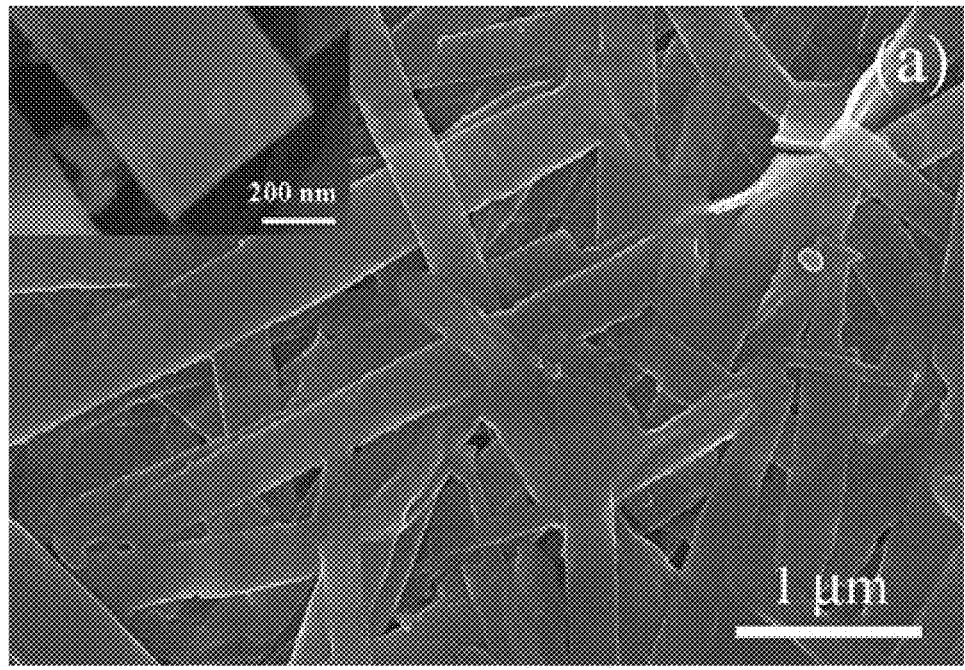
FIG. 2A shows an SEM image of Ru-LCE nanobelts ("NBs") and FIG. 2B shows a TEM image of Ru-LCE nanobelts ("NBs"). Insets in FIG. 2A and FIG. 2B show side-face SEM image and SAED pattern of single NB, respectively.
Figure 2B:
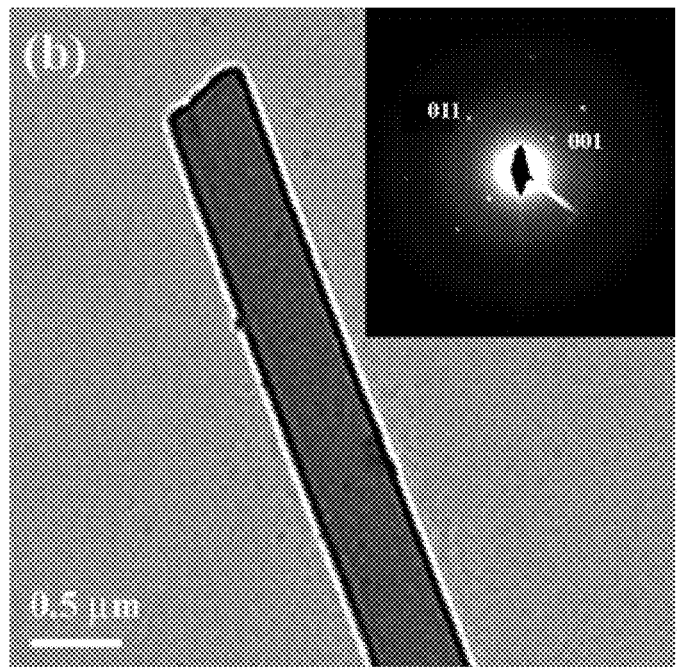

SEM and TEM images, as shown in FIG. 2A and FIG. 2B, indicate that the particles obtained after long time aging have a long, straight, belt-like morphology with widths of about 200 to 1000 nm and lengths of about 5 to 15 μm. FESEM (field-emission scanning electron microscopy) may also be used to characterize the NBs. The thickness of the NBs ranges from around 50 to 120 nm, as estimated from the side-face SEM image of NBs and the width-to-thickness ratios are about 5 to 10. The selected-area electron diffraction (SAED) pattern (inset in FIG. 2B) reveals that the as-prepared NBs have single crystal structures and grow along the [001] direction. This is also confirmed by the contrast of the X-ray diffraction (XRD) pattern which indicates the preferential orientation of [001] lattice planes in the NBs. The strong and sharp XRD signals suggest a highly crystalline structure of Ru-LCE NBs, and the main peak at 2.231° corresponds to the preferential [001] growth plane of the Ru-LCE single crystal. According to cell volume and NB size (10000×500×100 nm), a single NB contains about 3.0×10$^8$ Ru-LCE molecules.

Compared to the usual nanowires with a round cross-section, a nanobelt structure should provide large area interface when deposited on electrodes, thus facilitating the fabrication of devices with improved electrical contact.

Figure 3A:
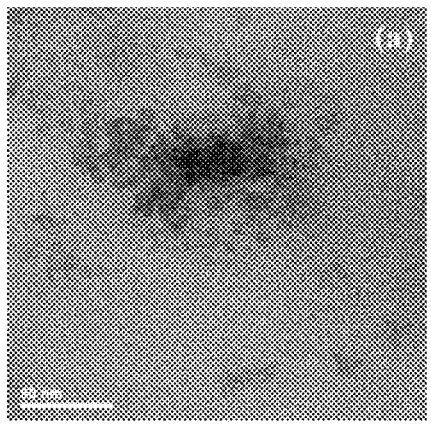
FIG. 3A, FIG. 3C, and FIG. 3D show TEM images
Figure 3B:
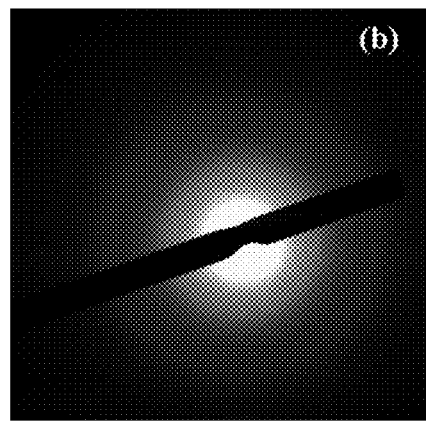
FIG. 3B shows SAED pattern of Ru-LCE samples obtained at room temperature in early stages after re-precipitation.
Figure 3C:
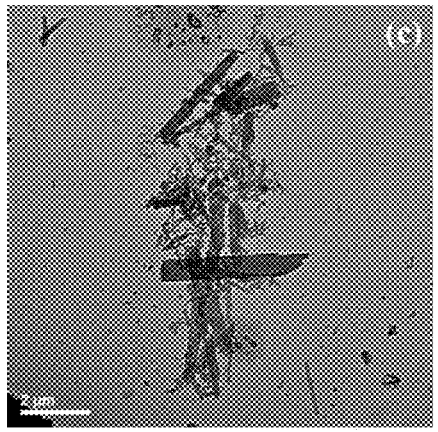
Figure 3D:
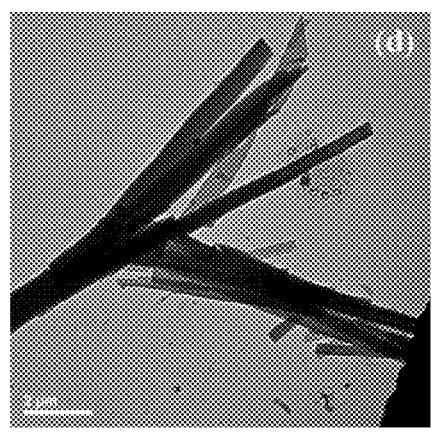

Samples collected 5 min after injection consisted of about 10 nm sized NPs of amorphous Ru-LCE (see FIG. 3A and FIG. 3B), which subsequently aggregated within 30 min into a belt-like structure (see FIG. 3C). Extending the aging time to 2 hours resulted in a progressive increase in the length of the NBs (see FIG. 3D). Electron-diffraction analysis indicated that the initially-formed NB was amorphous Ru-LCE. Extending the aging time to 24 h resulted in a progressive increase in the crystallinity of the NBs. Without being bound by theory, according to the above observations, formation of Ru-LCE single-crystalline NBs involves a multi-step process involving nucleation, oriented assembly and restructuring of initially formed NP building blocks, rather than direct growth from solution according to classical mechanisms of crystallization.

Figure 4A:
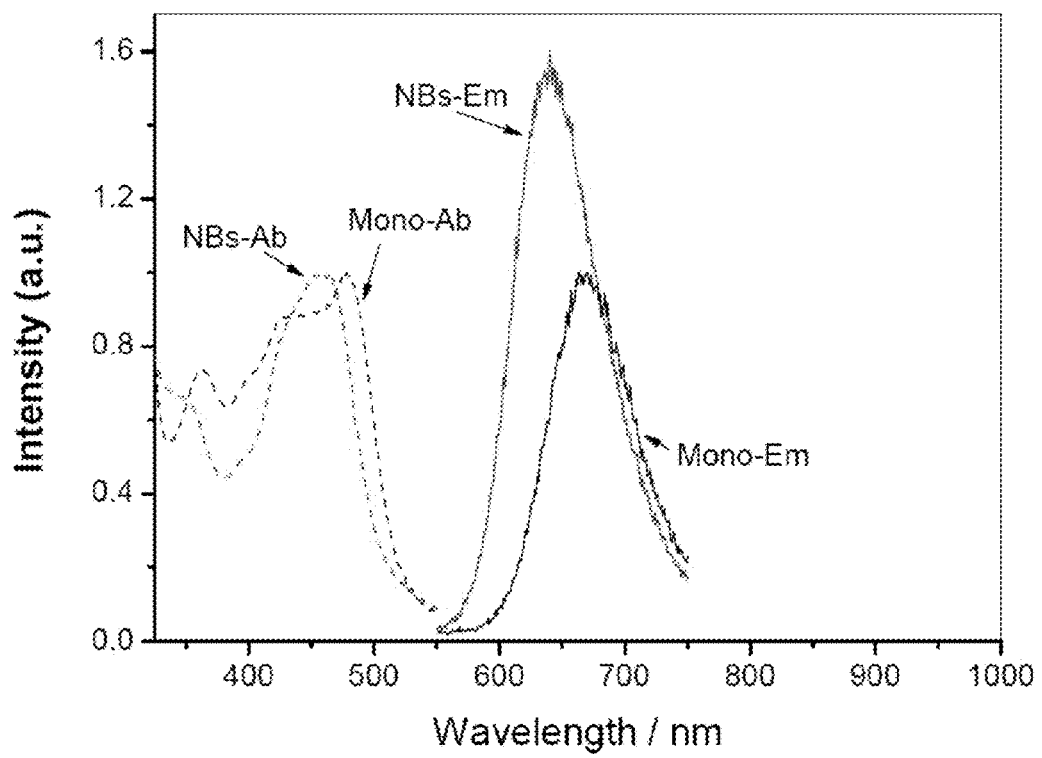
FIG. 4A shows normalized absorption (dashed) and fluorescence emission (solid) spectra of Ru-LCE NBs ("NBs-Ab" and "NBs-Em" respectively) in water and normalized absorption (dashed) and fluorescence emission (solid) spectra of Ru-LCE monomers in MeCN (i.e., Ru-LCE molecules in solution; "Mono-Ab" and "Mono-Em" respectively). Concentrations of Ru-LCE monomers and NBs are $6.75 \times 10^{-6}$ M and $2.25 \times 10^{-14}$ M, respectively.
Figure 4B:
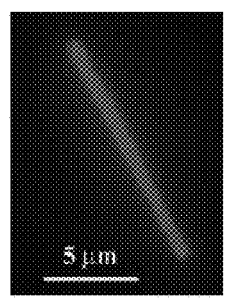
FIG. 4B is fluorescence image of single NB.

FIG. 4A shows a comparison of absorption and fluorescence emission spectra of Ru-LCE NBs and the corresponding monomers in solution. The monomer in MeCN exhibits a wide intramolecular charge-transfer absorption band (360 to 480 nm), which is assigned to the metal to ligand charge transfer (MLCT) transition (that is dπ→π*). The lowest-energy metal to ligand charge transfer transition of NBs in aqueous solution exhibits an obvious blue-shift (from 480 to 458 nm) as compared to monomers in acetonitrile, suggesting the formation of H-aggregates in the NBs due to strong π-stacking interactions. The fluorescence spectra of the NBs also show a similar hypsochromic shift as the absorption spectra and an enhanced fluorescence emission (at about 640 nm), implying that the NBs are J-aggregates, where the molecules are arranged in a head-to-tail direction, inducing a relatively high fluorescence efficiency. The fluorescence image of a NB can be easily observed (see FIG. 4B). Without being bound by theory, it is believed that the co-existence of two kinds of aggregates (H- and J-type) leads to spontaneous formation of the NBs.

Figure 5A:
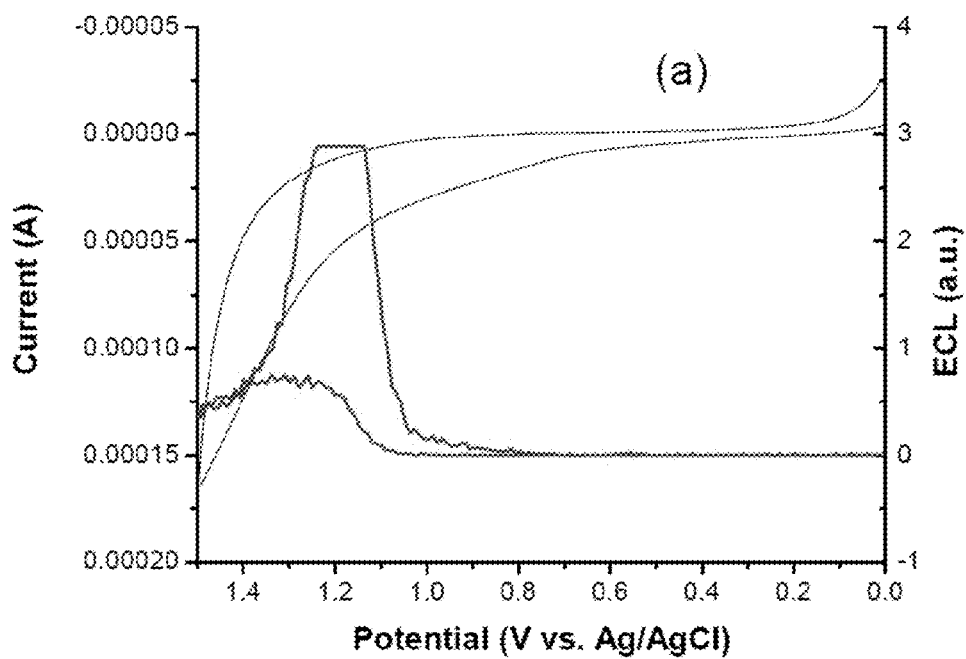
FIG. 5A shows cyclic voltammogram ("CV") and ECL curve of Ru-LCE NB suspension.
Figure 5B:
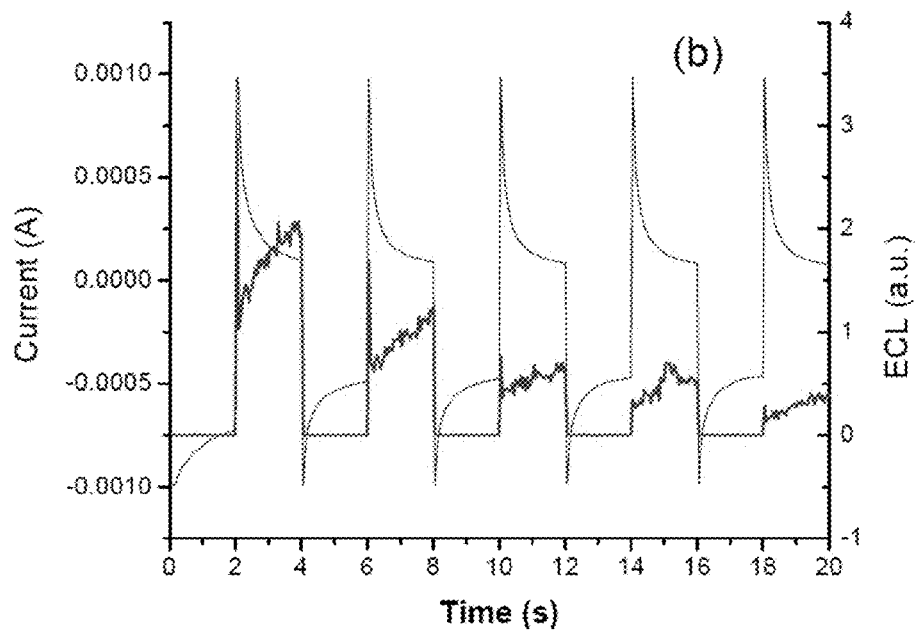
FIG. 5B shows current and ECL for potential steps between −1.25 V and 1.25 V. Step durations are 2, 6, 10, 14 and 18 seconds at each potential. Supporting electrolyte and co-reactant are 0.1 M phosphate buffer solution (pH 7.2) and 0.1 M tripropyl amine ("TPrA"), respectively. Concentration of NBs is $2.2 \times 10^{-14}$ M. Platinum electrode, 1.5 mm, (FIG. 5A) potential scan rate, 0.1 V/s and (FIG. 5B) pulse width, 2 seconds.
Figure 6A:
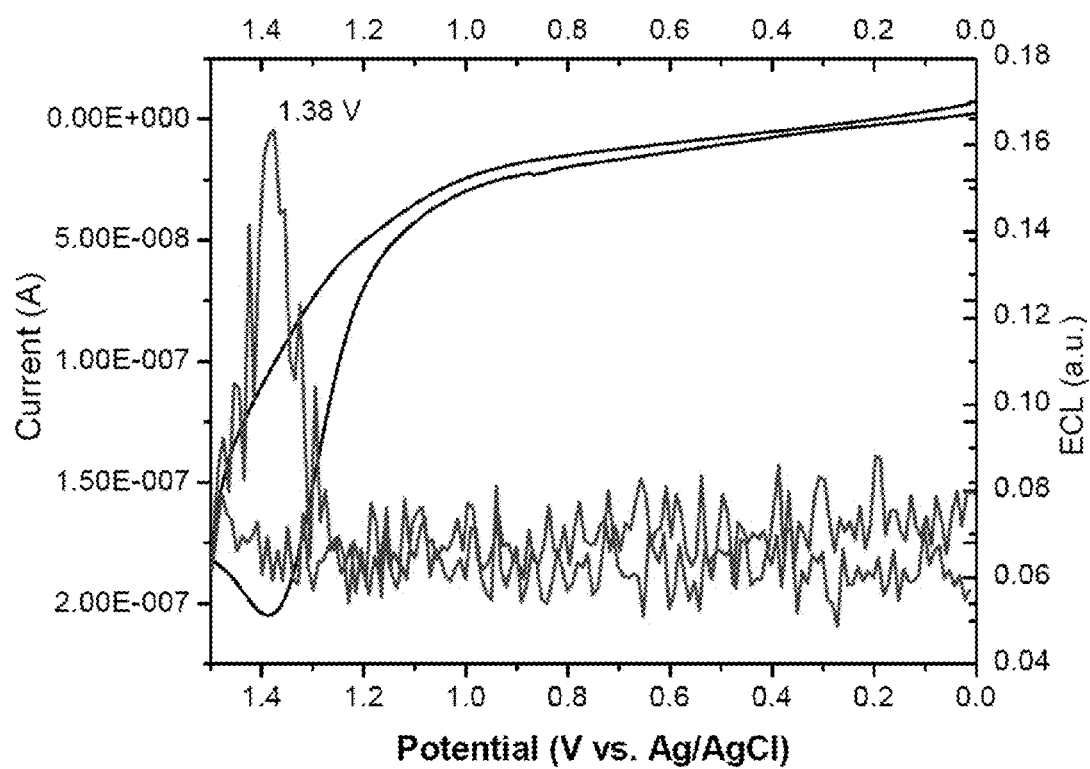
FIG. 6A shows CV and ECL curve of single Ru-LC NB deposited on a platinum ultramicroelectrode (UME) in 0.1 M phosphate buffer solution (pH 7.2) containing 0.1 M TPrA. Potential scan rate, 0.1 V/s.
Figure 6B:
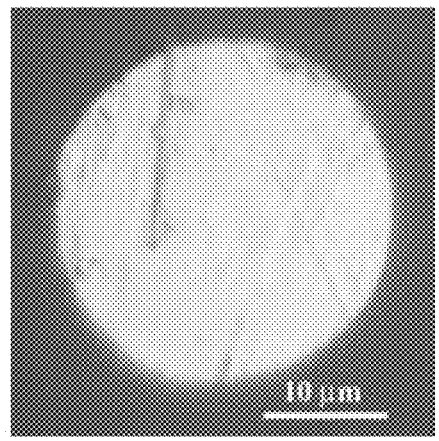
FIG. 6B is optical microscope image of UME with single NB.

Two methods were used to observe ECL of the NBs at a platinum electrode or an ultramicroelectrode (UME). First, ECL from the NBs dispersed in water containing 0.1 M tripropylamine (TPrA) as a co-reactant and 0.1 M phosphate buffer could be easily observed during potential scans (from 0 to 1.5 V) or pulses (−1.25 to 1.25 V) (see FIG. 5A and FIG. 5B). Second, the ECL curve of a single Ru-LCE NB deposited on a platinum UME was also observed (see FIG. 6A). The cyclic voltammogram (CV) shows a rather broad irreversible anodic wave due to the direct oxidation of TPrA, and the single Ru-LCE NB has little influence on the cyclic voltammogram (CV). The oxidation current begins at about 1.1 V peaks at potential of about 1.38 V, and is irreversible. Such anodic oxidation behavior is similar to that of TPrA in neutral, aqueous solutions at a glassy carbon electrode. The mechanism likely follows that of Ru(bpy)$_3^{2+}$ in solution, where scanning the electrode potential positive of 1.25 V, causes the oxidation of Ru(bpy)$_2$(bpy-C$_{16}$Est)$^{2+}$ in the adsorbed NB to the +3 form, either directly, or via TPrA radical cations (illustrated in Schemes IIA and IIB below). Reaction of the +3 form with either the reducing TPrA radical or the +1 form produces the excited state. The ECL emission intensity increases with increasing potential. Note, that no ECL is observed for an aqueous solution that is saturated with Ru(bpy)$_2$(bpy-C$_{16}$Est)$^{2+}$ prepared by putting a slide with a film of this material (cast from an acetonitrile solution) in the solution overnight with gentle stirring.

Scheme IIA

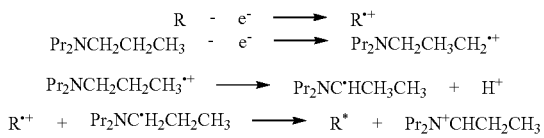

Scheme IIB

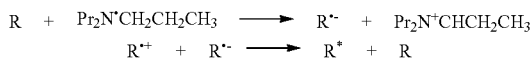

Rubrene NCs were prepared by a re-precipitation method as follows: 100 μL of 5 mM rubrene solution in tetrahydrofuran (THF) was quickly injected into 10 mL of deionized water under an argon atmosphere with vigorous stirring at room temperature. The resulting clear pale red NC solution was then filtered with a 0.22 μm filter. The hydrodynamic radius of rubrene NPs in water determined by dynamic light scattering (DLS) is about 20 nm and there is a small amount of aggregates around 75-100 nm, in size. The kinetics of the formation of the aggregates is determined by the interaction between the particles, the particle size, and the flow conditions within system. Addition of capping agents, such as a low molecular weight surfactant or neutral or charged polymers can dramatically affect the formation and/or aggregation process of NPs. It can also stabilize the particles. For example, the addition of Triton X-100 in water favors the formation of very small rubrene NCs (~4 nm), and the size distribution is narrow.

Figure 7A:
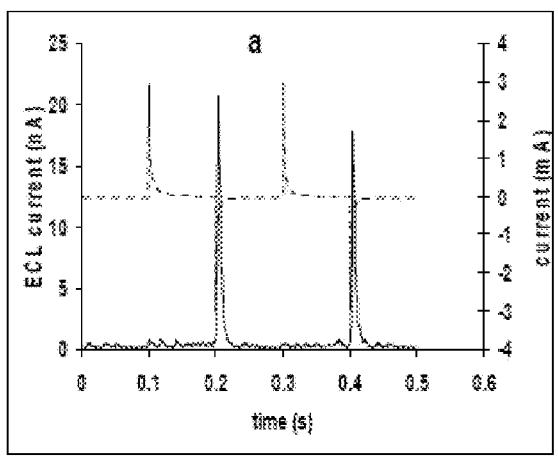
FIG. 7A shows chronoamperometry (dotted line) and transient ECL (solid line) for rubrene nanocrystals (NCs) (prepared from THF), 0.1 M TPrA, 0.1 M NaClO$_4$, pulse width 0.1 s (FIG. 7B) CV, sweeping ECL of rubrene NCs, blank experiment; 0.1 M TPrA, 0.1 M NaClO$_4$, scan rate: 500 mV/s.
Figure 7B:
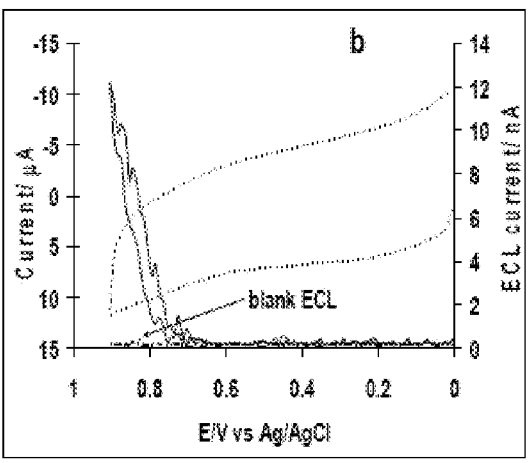
FIG. 7C shows chronoamperometry (dotted line) and transient ECL (solid line) for rubrene NCs (prepared from DMF), 0.1 M TPrA, 0.1 M NaClO$_4$, pulse width 0.1 s (FIG. 7D) Transient ECL (solid line) for rubrene NCs (prepared from THF), 0.1 M TPrA, 0.1 M NaClO$_4$, pulse width 0.05 second.
Figure 7C:
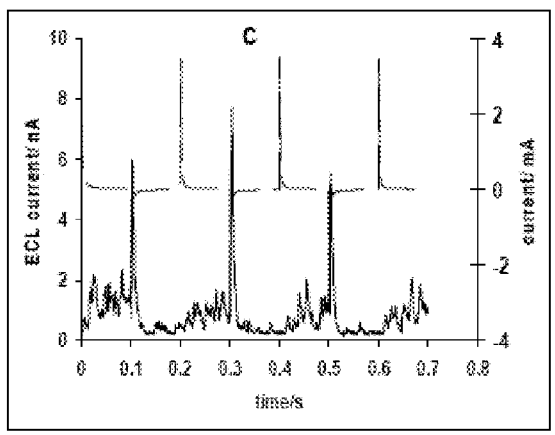
Figure 7D:
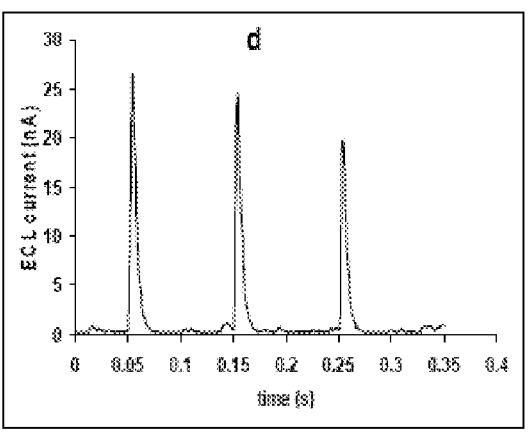

ECL from the rubrene NCs dispersed in water containing 0.1 M tripropylamine (TPrA) as a co-reactant and 0.1 M phosphate buffer could be easily observed during potential scans (from 0 to 0.9 V vs. Ag/AgCl) (see FIG. 7B) or pulses (0 to 1.1 V) (see FIG. 7A, FIG. 7C and FIG. 7D). The ECL signal during the potential pulse is observable but decays sharply with time within the pulse duration (faster than the normal diffusion-limited mass transfer rate) perhaps due to the instability of radical ions generated in water medium. The CV in the potential range shown in FIG. 7B is featureless, but will reach a diffusion-limited oxidation peak of TPrA at a positive potential (refer to FIG. 6A). Rubrene NCs prepared in different solvents, such as N,N-dimethylformamide DMF, show much lower ECL signal at the same condition of preparation, i.e. injection of 100 μL 5 mM rubrene in DMF into 10 mL of deionized water. Increasing the concentration of rubrene NCs 5 times increases the ECL signal, suggesting that solvent polarity and solubility of the organic or ionic compound in solvents could subtly affect the nanocrystallization process in the re-precipitation method.

NCs of DPA were prepared by using THF, DMF or MeCN as a good solvent and water as a poor solvent. The average hydrodynamic radius of DPA NCs using MeCN as the dissolving solvent is about 45 nm, which is considerably bigger than the rubrene NCs described above. An SEM image of the DPA NCs reveals that they are poly disperse nanorods with diameters from about 20 to 100 nm and lengths from about 100-600 nm (see FIG. 1).

Figure 8:
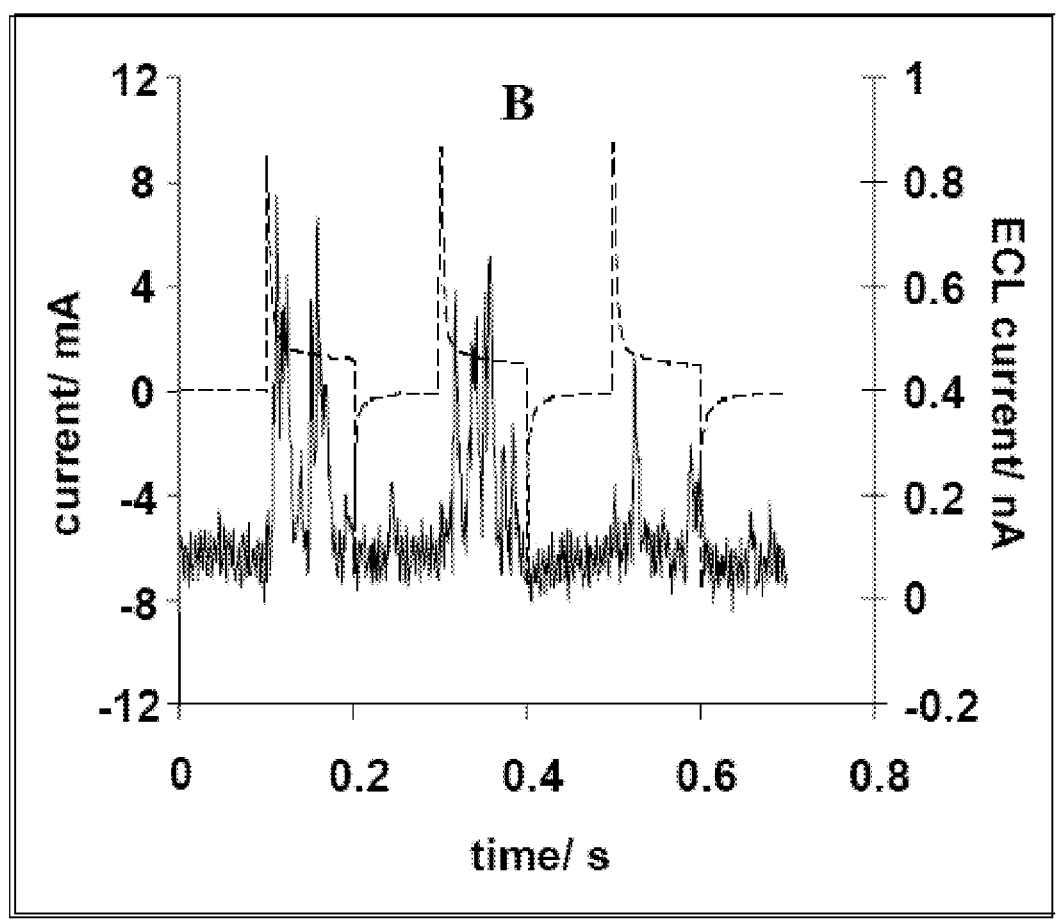
FIG. 8 shows ECL (solid line) and current (dotted line) of DPA nanorods in aqueous solution containing 0.1 M Na$_2$C$_2$O$_4$ (sodium oxalate) as the co-reactant.

ECL of DP A NCs was examined by comparing TPrA or oxalate as the co-reactant. No significant ECL intensity from DPA NCs was observed by using TPrA as the co-reactant while some ECL was detected in the presence of oxalate as shown in FIG. 8. This is consistent with published reports, showing that $CO_2^-$ (the active intermediate produced during oxalate oxidation) is more energetic than TPrA (the active intermediate generated from TPrA oxidation). It is believed that the scheme depicted in Scheme 1 may illustrate the scheme by which a co-reactant (e.g., TPrA) may interact with the redox active luminescent compounds in the present nanostructured materials to generate an excited state luminescent species capable of emitting light.

Organic or ionic (e.g., organometallic compounds or metal-ligand complexes) nanostructured materials, such as NSMs, have been synthesized and their ECL has been examined using Ru-LCE, rubrene, and DPA as the indicators and TPrA or oxalate as a co-reactant. The skilled artisan will recognize that other NPs, co-reactants and other solvent combinations may be used. In order to reduce the background current and enhance the relative ECL efficiency, an electrode or the NPs can undergo certain surface treatments. Suitable electrodes may be formed from materials such as ITO, gold, glassy carbon, boron-doped diamond, and other like materials.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; ethers; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups can be substituted one or more times with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, cyclopentadienyl, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 5-14 carbons, and in others from 5 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, bipyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl,azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like.

Representative substituted alkoxy groups can be substituted one or more times with substituents such as those listed above.

Illustrative Embodiments

While the making and using of various embodiments of the present invention are discussed in detail herein, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

One embodiment provides a nanostructured particulate material formed from a redox active luminescent compound. The nanostructured material commonly has a least one dimension which has an average size no larger than about 250 nm, more commonly no more than about 150 nm and, in some embodiments, at least one dimension may have an average size no larger than about 100 nm. For example, the nanostructured material may be a nanoparticle ("NP") in which no dimension has an average size larger than about 200 nm. Other examples include nanocrystals ("NCs") in which, typically, at least two and, often three, dimensions are no more than about 200 nm and commonly no more than about 100 nm. Other embodiments may include nanobelts ("NBs"), which have long, straight and belt-like morphology, with a width of at least about 150 nm and a thickness of about 50 to 125 nm. Such nanobelts may have widths of about 200 to 1000 nm and lengths of about 5 to 15 μm, and typically have a width-to-thickness ratio of about 5 to 10 and may have an aspect ratio of about 10 or more. In still other embodiments, the nanostructured material may be a nanorod having an average diameter of no more than about 250 nm, commonly about 10 to 150 nm, and an average length of about 50 nm to 1 micron.

One embodiment provides a method for detecting an analyte in a sample solution to which luminescent nanostructured particulate materials have been added. The method includes contacting the sample solution with an electrochemical cell containing two or more electrodes in communication with the solution; and generating one or more ECL properties through an interaction of the luminescent nanostructured materials, the liquid sample and two or more of the electrodes; and measuring at least one ECL property generated by the interaction. The luminescent nanostructured materials include a redox active luminescent organic or organometallic compound.

Another embodiment provides a method of determining the presence of an analyte of interest comprising:
 (a) contacting the analyte with a chemical moiety under suitable conditions so as to form a reagent mixture; wherein the chemical moiety includes a nanostructured particulate material comprising a redox active luminescent organic or organometallic compound;
 (b) inducing the chemical moiety to emit electromagnetic radiation by exposing the reagent mixture to chemical or electrochemical energy; and
 (c) detecting the emitted electromagnetic radiation and thereby determining the presence of the analyte of interest.

Suitable redox active luminescent compounds, which can be used to form the present nanostructured materials, can be selected from a variety of organic and/or ionic luminescent compounds. Examples include luminescent aromatic hydrocarbons, e.g., luminescent phenyl substituted aromatic hydrocarbons such as phenyl substituted polycyclic aromatic compounds, and luminescent metal-containing complexes, e.g., heteroaromatic polydentate complexes of a metal ion such as ruthenium.

Examples of suitable phenyl substituted polycyclic aromatic compounds, often in the form of nanostructured luminescent materials (which may be in the form of nanocrystals or nanorods), include rubrene ("Rub"), diphenylanthracene ("DPA") and other luminescent phenyl substituted polycyclic aromatic compounds. Heteroaromatic polydentate complexes include aromatic compounds with one or more heteroatoms in which the complex may bind more than one metal or may bind more than once to a single metal.

Examples of suitable luminescent metal-containing complexes include polydentate complexes of a metal ion such as ruthenium, osmium, rhenium, cerium, europium, terbium, and/or ytterbium. Particular examples of suitable heteroaromatic polydentate complexes include a substituted bis(2,2'-bipyridyl)ruthenium(II) or tris(2,2'-bipyridyl)ruthenium(II) containing moieties, wherein at least one of the bipyridyl ("bpy") groups is substituted with one or more long chain alkyl groups.

Suitable long chain alkyl substituted bpy groups ("LCsub-bpy") include: 4-methyl-4'-alkanoylaminomethyl-2,2'-bipyridines; 4,4'-bis-(alkoxymethyl)bipyridines; 4,4'-bis-(alkylmercaptomethyl)bipyridines; alkyl esters of omega-(4-methyl-2,2-bipyridine-4'-yl)-alkanoic acids; di-n-alkyl 4,4'-bis-(carboxylate)bipyridines; n-alkyl diesters of 4,4'-bis-(carboxy)-2,2-bipyridines; and diesters of long chain fatty acid with 4,4'-bis-(hydroxymethyl)bipyridines.

Examples of suitable luminescent metal complexes, including n-alkyl diesters of 4,4'-bis-(carboxy)-2,2-bipyridines, include Ru(II) bis(2,2'-bipyridine)(di-n-alkyl 4,4'-bis-(carboxylate)bipyridine)$^{2+}$ salts, e.g., Ru(II) bis(2,2'-bipyridine)(di-n-pentadecyl 4,4'-bis-(carboxylate) bipyridine)$^{2+}$ salts or other related ruthenium complexes, where the alkyl ester group each contain about 10 to 25 carbon atoms. Suitable examples of such alkyl ester groups include such esters of stearyl alcohol, palmityl alcohol and dodecyl alcohol.

Examples of suitable luminescent metal complexes based on 4-methyl-4'-alkanoylaminomethyl-2,2'-bipyridines include Ru(II) bis(2,2'-bipyridine)(4-methyl-4'-alkanoylaminomethyl-2,2'-bipyridine)$^{2+}$ salts, e.g., Ru(II) bis(2,2'-bipyridine)(4-methyl-4'-stearoylaminomethyl-2,2'-bipyridine)$^{2+}$ salts.

Examples of suitable luminescent metal complexes based on 4,4'-bis-(alkoxymethyl)bipyridines include Ru(II) bis(2,2'-bipyridine)(4,4'-bis-(n-alkoxymethyl)bipyridine)$^{2+}$ salts e.g., Ru(II) bis(2,2'-bipyridine)(4,4'-bis-(n-hexadecyloxymethyl)bipyridine)$^{2+}$ salts.

Examples of suitable luminescent metal complexes based on 4,4'-bis-(alkyl mercaptomethyl)bipyridines include Ru(II) bis(2,2'-bipyridine)(4,4'-bis-(n-alkylmercaptomethyl)bipyridine)$^{2+}$ salts e.g., Ru(II) bis(2,2'-bipyridine)(4,4'-bis-(n-alkylmercaptomethyl)bipyridine)$^{2+}$ salts.

Other examples of suitable luminescent metal complexes based on alkyl esters of omega-(4-methyl-2,2-bipyridine-4'-yl)-alkanoic acids include Ru(II) bis(2,2'-bipyridine)(4-methyl-2,2-bipyridine-4'-yl)-alkanoic acid alkyl ester)$^{2+}$ salts, e.g., Ru(II) bis(2,2'-bipyridine)4-(4-methyl-2,2-bipyridine-4'-yl)-butyric acid decyl ester)$^{2+}$ salts. Additional examples include Ru(II) bis(2,2'-bipyridine)(di-n-alkanoyl ester of 4,4'-bis-(hydroxymethyl)bipyridine)$^{2+}$ salts, e.g., Ru(II) bis(2,2'-bipyridine)(di-stearoyl ester of 4,4'-bis-(hydroxymethyl)bipyridine)$^{2+}$ salts; and Ru(II) bis(2,2'-bipyridine)(dipalmitoyl ester of 4,4'-bis-(hydroxymethyl)bipyridine)$^{2+}$ salts.

Another embodiment provides a method for detecting the presence of an analyte of interest in a liquid sample, the method comprising:
(a) contacting the sample with a reagent comprising a nanostructured material; wherein the reagent is capable of being induced to electrochemiluminesce repeatedly and the nanostructured material comprises a redox active luminescent organic and/or ionic compound;
(b) inducing the reagent to electrochemiluminesce repeatedly; and
(c) detecting the presence of luminescence emitted thereby detecting the presence of the analyte of interest in the sample. The method may also include contacting the sample with the reagent and an ECL coreactant, such as such as an oxalate salt (e.g., sodium oxalate) or a trialkylamine (e.g., tripropylamine). For example, in many embodiments of the method, the nanostructured material may include a polydendate metal complex (such as a ruthenium bipyridyl complex) and trialkylamine coreactant (e.g., tripropylamine). In other embodiments of the method, the nanostructured material may include a phenyl substituted polycyclic aromatic hydrocarbon (such as rubrene) and trialkylamine coreactant (e.g., tripropylamine). In still other embodiments of the method, the nanostructured material may include a phenyl substituted polycyclic aromatic hydrocarbon (such as diphenylanthracene) and an oxalate salt coreactant (e.g., sodium oxalate).

Another embodiment provides a method for quantitatively determining the amount of an analyte of interest present in a liquid sample, the method comprising: (a) contacting the sample with a reagent comprising a nanostructured material; wherein the reagent is capable of being induced to electrochemiluminesce repeatedly; (b) inducing the reagent to electrochemiluminesce repeatedly; and (c) determining the amount of luminescence emitted and thereby quantitatively determining the amount of the analyte of interest present in the sample. The nanostructured material typically includes a redox active luminescent organic and/or ionic compound. The method may also include contacting the sample with the reagent and an ECL coreactant, such as such as sodium oxalate or trialkylamine (e.g., tripropylamine).

Another embodiment provides a method for detecting the presence of an analyte of interest in a liquid sample, the method comprising:
(a) contacting the sample with a reagent comprising a nanostructured material; wherein the reagent is capable of being induced to electrochemiluminesce repeatedly and the nanostructured material comprises a redox active luminescent organic and/or organometallic compound;
(b) inducing the reagent to electrochemiluminesce repeatedly; and
(c) detecting the presence of luminescence emitted thereby detecting the presence of the analyte of interest in the sample. The method may also include contacting the sample with the reagent and an ECL coreactant, such as an oxalate salt (e.g., sodium oxalate) or trialkylamine (e.g., tripropylamine).

Another embodiment provides a method for quantitatively determining the amount of an analyte of interest present in a liquid sample, the method comprising: (a) contacting the sample with a reagent comprising a nanostructured material; wherein the reagent is capable of being induced to electrochemiluminesce repeatedly; (b) inducing the reagent to electrochemiluminesce repeatedly; and (c) determining the amount of luminescence emitted and thereby quantitatively determining the amount of the analyte of interest present in the sample. The nanostructured material typically includes a redox active luminescent organic and/or ionic compound. The method may also include contacting the sample with the reagent and an ECL coreactant, such as such as sodium oxalate or trialkylamine (e.g., tripropylamine).

Another embodiment provides a method of determining the presence of an analyte of interest in a sample comprising:
(a) contacting the sample with a chemical moiety under suitable conditions so as to form a reagent mixture; wherein the chemical moiety includes a nanostructured particulate material comprising a redox active luminescent compound;
(b) inducing the chemical moiety to emit electromagnetic radiation; and
(c) detecting the emitted electromagnetic radiation and thereby determining the presence of the analyte of interest;
wherein inducing the chemical moiety to emit electromagnetic radiation comprises exposing the reagent mixture to chemical, electrochemical and/or electromagnetic energy; and
the redox active luminescent compound includes a luminescent polycyclic aromatic hydrocarbon, such as a phenyl substituted polycyclic aromatic hydrocarbon. The reaction mixture may also include an ECL coreactant, such as sodium oxalate, persulfate, benzoyl peroxide, or a trialkylamine (e.g., tripropyl amine).

The nanostructured material comprising luminescent polycyclic aromatic hydrocarbon may be in the form of redox active, luminescent nanoparticles having an average hydrodynamic radius of no more than about 100 nm. Such nanoparticles maybe formed from a phenyl substituted polycyclic aromatic hydrocarbon such as rubrene. For example, nanocrystals formed from phenyl substituted polycyclic aromatic hydrocarbons may have a hydrodynamic radius of no more than about 50 nm (as determined as a dispersion in water determined by dynamic light scattering (DLS)) which may also include a small amount of nanocrystal aggregates around 75-100 nm in size. In other embodiments, the nanostructured material comprising luminescent polycyclic aromatic hydrocarbon may be in the form of nanorods, e.g., nanorods having a diameter of about 10 to 150 nm and a length of about 50 nm to 1 micron. Such nanorods maybe formed from a phenyl substituted polycyclic aromatic hydrocarbon such as diphenylanthracene. Nanorods may be formed diphenylanthracene may have a diameter of about 20 to 100 nm and a length of about 100 nm to 600 nm.

A method of determining the presence of an analyte of interest in a sample comprising:
(a) contacting the sample with a chemical reagent under suitable conditions so as to form a reagent mixture; wherein the chemical reagent includes a nanostructured particulate material comprising a redox active luminescent compound;
(b) inducing the chemical reagent to emit electromagnetic radiation; and
(c) detecting the emitted electromagnetic radiation and thereby determining the presence of the analyte of interest;
wherein inducing the chemical reagent to emit electromagnetic radiation comprises exposing the reagent mixture to chemical, electrochemical and/or electromagnetic energy; and
the redox active luminescent compound includes a polydendate metal complex, such as a bipyridyl containing metal complex. The reaction mixture may also include an ECL coreactant, such as oxalate salt, persulfate salt, benzoyl peroxide, or a trialkylamine (e.g., tripropyl amine).

The nanostructured particulate material comprising the redox active luminescent compound may includes a redox active, luminescent polydendate metal complex, such as a luminescent heteroaromatic polydendate metal complex. Examples of suitable luminescent heteroaromatic polydendate metal complexes may include a ruthenium, osmium, rhenium, cerium, europium, terbium and/or ytterbium ion. Suitable nanostructured materials comprising polydendate metal complexes include luminescent nanobelts formed from heteroaromatic polydendate metal complexes containing one or more long chain alkyl substituted ligands. One examples of such nanostructured materials are nanobelts formed from heteroaromatic polydendate ruthenium complexes which include at least one long chain alkyl substituted bipyridine ligand. Such nanobelts can have widths of about 200 to 1000 nm and lengths of about 5 to 15 μm. The thickness of these nanobelts can range from around 50 to 120 nm (as characterized by field-emission scanning electron microscopy).

Other embodiments are directed to methods which employ nanostructured particulates formed from redox active, luminescent polycyclic aromatic hydrocarbon. Such nanostructured particulates commonly have a least one dimension which has an average size no larger than about 250 nm and, in some instances, no larger than about 100 nm.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the present invention.

What is claimed is:

1. 9,10-Diphenvlanthracene nanorods; wherein the nanorods have a least two dimensions which are no larger than about 200 nm.

2. The nanorods of claim 1, wherein the nanorods are substantially free of surfactant.

3. The nanorods of claim 1, wherein the nanorods can be induced to repeatedly emit electromagnetic radiation by direct exposure to an electrochemical energy source.

4. The nanorods of claim 1, wherein the nanorods have an average hydrodynamic radius of no more than about 100 nm.

5. The nanorods of claim 1, wherein the 9,10-diphenylanthracene nanorods have a diameter of about 10 to 150 nm and a length of about 50 nm to 1 micron.

6. The nanorods of claim 1, wherein the nanorods are polydisperse 9,10-diphenylanthracene nanorods with diameters of about 20 to 100 nm and lengths of about 100 to 600 nm.

7. The nanorods of claim 1, wherein the 9,10-diphenylanthracene nanorods have an average hydrodynamic radius of about 45 nm.

8. Nanorods having a least two dimensions which are no larger than about 200 nm wherein nanorods are formed by a process which comprises injecting a 9,10-diphenylanthracene solution in organic solvent into deionized water; wherein the organic solvent is acetonitrile, tetrahydrofuran, and/or N,N-dimethylformamide.

9. The nanorods of claim 8, wherein the organic solvent is acetonitrile.

10. The nanorods of claim 1, wherein the nanorods are formed by a process which comprises injecting a solution of 9,10-diphenylanthracene in organic solvent into deionized water.

11. The nanorods of claim 1 comprising polydisperse nanorods consisting essentially of 9,10-diphenylanthracene, wherein the nanorods have an average diameter of about 10 to 150 nm and an average length of about 50 nm to 1 micron.

12. The nanorods of claim 11, wherein the polydisperse nanorods are substantially free of surfactant.

13. The nanorods of claim 8, wherein the nanorods are polydisperse nanorods consisting essentially of 9,10-diphenylanthracene, wherein the nanorods have an average diameter of about 10 to 150 nm and an average length of about 50 nm to 1 micron.

14. The nanorods of claim 8, wherein the nanorods have an average hydrodynamic radius of no more than about 100 nm.

15. The nanorods of claim 8, wherein the nanorods have an average hydrodynamic radius of about 45 nm.

16. The nanorods of claim 8, wherein the nanorods are polydisperse 9,10-diphenylanthracene nanorods with diameters of about 20 to 100 nm and lengths of about 100 to 600 nm.

17. The nanorods of claim 8, wherein the nanorods are substantially free of surfactant.

\* \* \* \* \*